(12) United States Patent
Hara

(10) Patent No.: US 10,881,352 B2
(45) Date of Patent: Jan. 5, 2021

(54) MULTIPLE-ELECTRODE GUIDE CATHETER FOR USE IN PERIPHERAL VESSEL

(71) Applicant: INTER NOVA INC, Tokyo (JP)

(72) Inventor: Hiroshi Hara, Tokyo (JP)

(73) Assignee: INTER NOVA INC, Tokyo (JP)

( * ) Notice: Subject to any disclaimer, the term of this patent is extended or adjusted under 35 U.S.C. 154(b) by 946 days.

(21) Appl. No.: 15/332,466

(22) Filed: Oct. 24, 2016

(65) Prior Publication Data
US 2017/0273627 A1    Sep. 28, 2017

(30) Foreign Application Priority Data

Mar. 28, 2016 (JP) .................................. 2016-063083

(51) Int. Cl.
| | | |
|---|---|---|
| A61B 5/00 | (2006.01) | |
| A61B 5/042 | (2006.01) | |
| A61B 5/0464 | (2006.01) | |
| A61N 1/05 | (2006.01) | |
| A61N 1/362 | (2006.01) | |

(52) U.S. Cl.
CPC .......... *A61B 5/6852* (2013.01); *A61B 5/0422* (2013.01); *A61B 5/0464* (2013.01); *A61N 1/056* (2013.01); *A61N 1/3622* (2013.01); *A61N 2001/0585* (2013.01)

(58) Field of Classification Search
CPC ..... A61B 5/042; A61B 5/0421; A61B 5/0422; A61B 5/6846; A61B 5/6851; A61B 18/1492; A61N 1/05; A61N 1/056; A61N 1/0587

See application file for complete search history.

(56) References Cited

U.S. PATENT DOCUMENTS

| | | | |
|---|---|---|---|
| 5,699,796 A | 12/1997 | Littmann et al. | |
| 5,857,997 A * | 1/1999 | Cimino | A61B 5/0422 |
| | | | 604/95.01 |
| 5,863,291 A | 1/1999 | Schaer | |

(Continued)

FOREIGN PATENT DOCUMENTS

| | | |
|---|---|---|
| GB | 2496788 | 5/2013 |
| JP | 2010-51516 | 3/2010 |

(Continued)

*Primary Examiner* — Eun Hwa Kim
(74) *Attorney, Agent, or Firm* — Duane Morris LLP; Gregory M. Lefkowitz; Jason M. Nolan

(57) ABSTRACT

Provided is a multiple-electrode monorail guide catheter for use in vascular insertion, including: an elongated catheter main body having a proximal end and a distal end; a guidewire inlet opening on the distal end; a guidewire outlet opening; an operation tube; a terminal unit on the proximal end; an electrode assembly having a double-lumen structure composed of an outer tube having electrodes on an outer surface of the outer tube and an inner tube independently provided from the outer tube, allowing insertion of a guidewire, having an outer diameter smaller than an inner diameter of the outer tube, and being accommodated within an outer tube lumen; a clearance defined by the outer tube luminal surface and an inner tube outer circumferential surface; and lead wires extending from the electrodes to the terminal unit on the proximal end and being inserted into the lumen of the outer tube.

12 Claims, 4 Drawing Sheets

(56) References Cited

U.S. PATENT DOCUMENTS

| | | | |
|---|---|---|---|
| 7,993,481 B2 * | 8/2011 | Hastings | A61B 5/0422 156/272.2 |
| 9,314,208 B1 * | 4/2016 | Altmann | A61B 5/6858 |
| 2001/0023365 A1 | 9/2001 | Medhkour et al. | |
| 2005/0070847 A1 * | 3/2005 | van Erp | A61M 25/0029 604/103.04 |
| 2006/0184011 A1 | 8/2006 | Macaulay et al. | |
| 2012/0065633 A1 * | 3/2012 | Yagi | A61B 18/04 606/28 |

FOREIGN PATENT DOCUMENTS

| | | |
|---|---|---|
| JP | 2012-75800 | 4/2012 |
| WO | 96/36277 | 11/1996 |
| WO | 03/034932 | 5/2003 |
| WO | 2013/101632 | 7/2013 |

\* cited by examiner

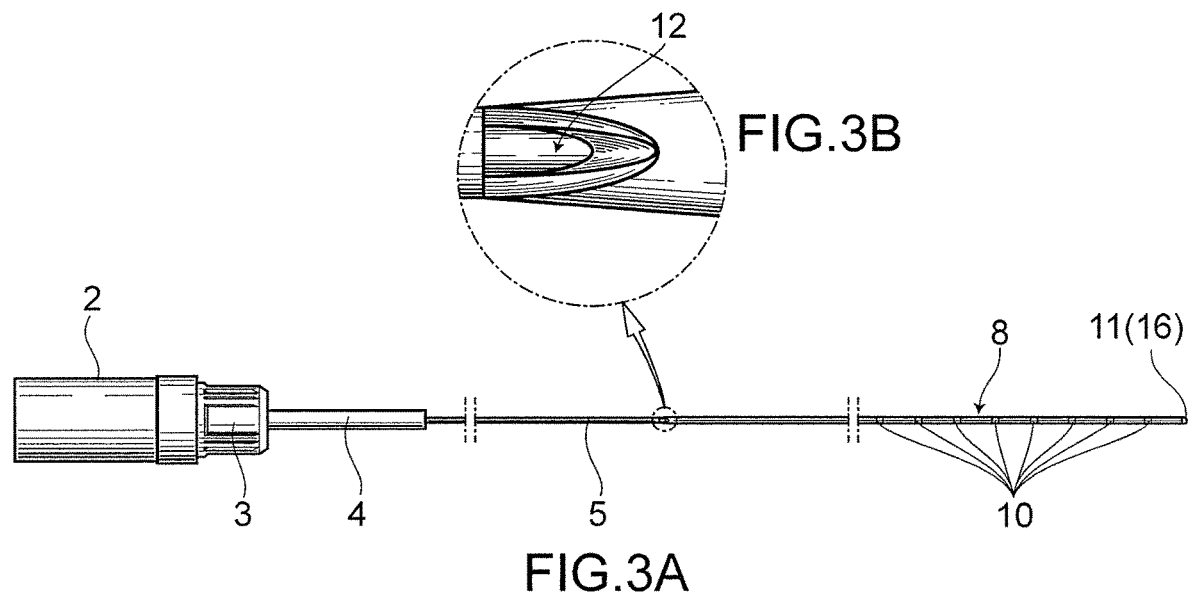
FIG.3A
FIG.3B
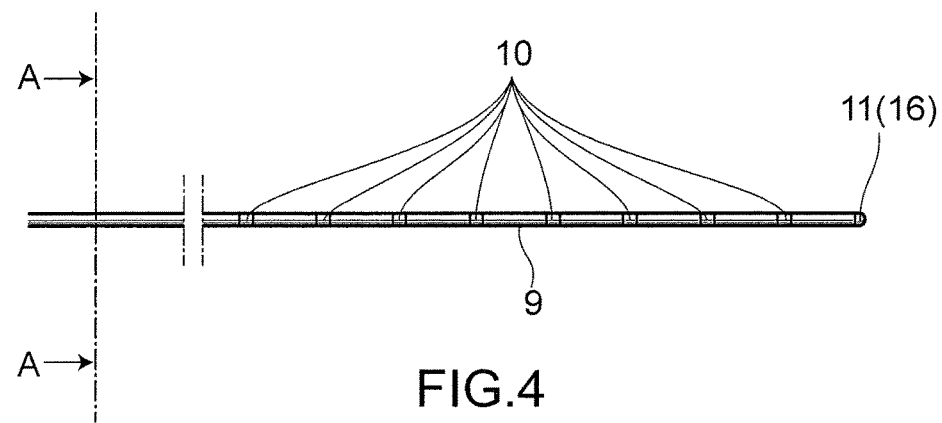
FIG.4
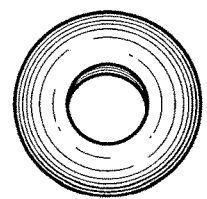
FIG.5

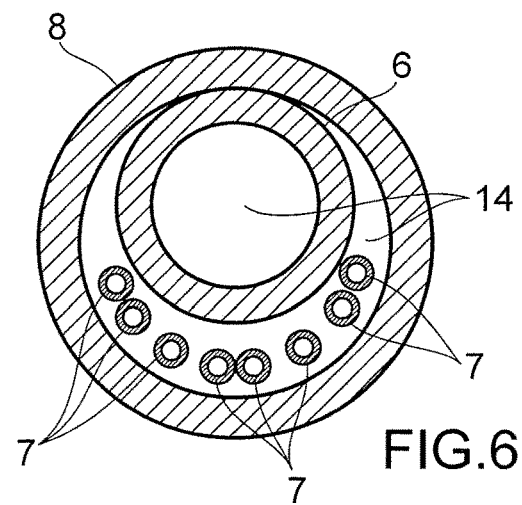
FIG.6
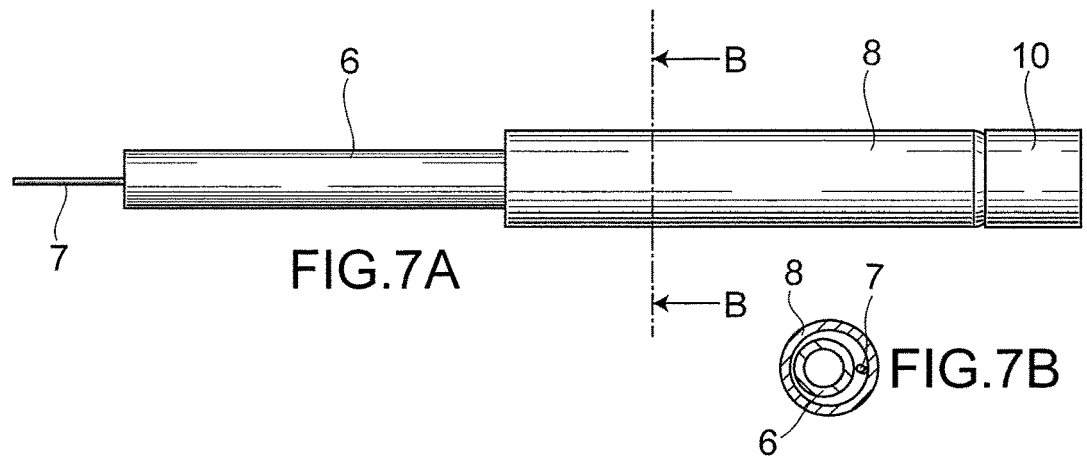
FIG.7A
FIG.7B
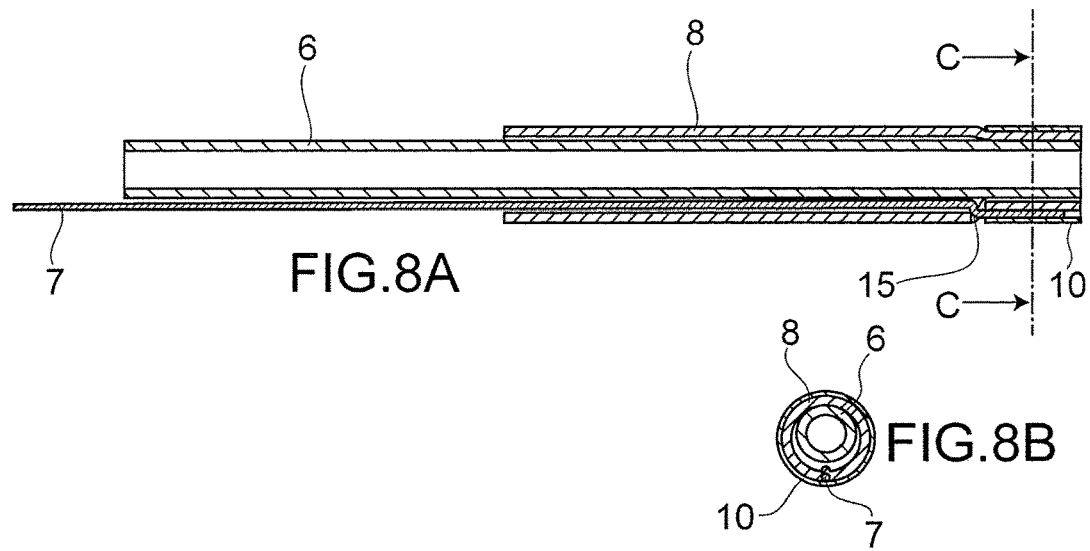
FIG.8A
FIG.8B

MULTIPLE-ELECTRODE GUIDE CATHETER FOR USE IN PERIPHERAL VESSEL

CROSS-REFERENCE TO RELATED APPLICATIONS

This application claims priority to Japanese Patent Application No. 2016-063083, filed Mar. 28, 2016, the entire contents of which are incorporated herein by reference.

TECHNICAL FIELD

The present invention relates to a monorail guide catheter that is insertable into small peripheral vessels such as coronary veins, and is provided with multiple electrodes for pacing and/or mapping. The present invention also relates to a production method of the monorail guide catheter.

BACKGROUND ART

There have been utilized small-diameter electrode catheters for the purpose of diagnosis of arrhythmias by cardiac electrophysiological testing. Such catheters are allowed to be inserted into the heart, particularly into coronary veins to measure electric potentials inside the coronary veins and to deliver electrical stimuli thereto in order to examine cardiac stimulus conduction system, or developmental mechanism of tachycardia circuit. Through catheterization study of blood vessels that are more peripherally located, there can be identified the site to be treated in an accurate manner. To achieve that, a catheter having a more reduced diameter needs to be used. Accurate diagnosis also contributes to the reduction in invasiveness caused by the treatments of patients.

In order to ease the burden on patients during catheter insertion, such catheters need to have excellent maneuverability for inserting the catheters in less time such that the electrodes thereof are allowed to reach a target site in a shorten time.

As conventional arts to achieve such purpose, there have been known some prior arts as disclosed in WO96/36277, JP2010051516 and JP2012075800 relating to cardiovascular catheters equipped with electrodes for the purposes of pacing and/or mapping. Unfortunately, the catheter of WO96/36277 has poor operability because no guidewire is used for the catheter. For this reason, a substantial amount of time is required for the catheter to be inserted into a vascular affected site of a patient, resulting in discontinuation of sales for safety concerns in many countries including Japan.

Regarding catheters as disclosed in JP2010051516 and JP2012075800, catheters having external diameters not smaller than 0.98 mm are currently in production and commercially available in Japan. Unfortunately, due to structural restriction associated with their small tube diameters, there is a need to integrally mold a tube having two lumens respectively corresponding to a lumen for insertion of lead wire and a lumen for insertion of guide wire, as shown in FIG. 1.

Further, in order to prevent blood vessel damages caused by friction against a blood vessel wall while sliding a catheter inside an intravascular lumen, there need to be eliminated steps defined by differences in level between electrodes and an outer circumferential surface of the catheter during a production step after mounting the electrodes. These steps in conventional catheters have heretofore been leveled through coating the same with resins as illustrated in WO03/034932. As the result, there arises a problem that the outer diameters of the electrode-equipped portions are made larger than the other portions of the catheter.

As for the method of coating the steps, defined by differences in level between the electrodes and outer circumferential surface of the catheter, with resin, the presence of resin coated portion needs spacing the electrodes far enough from each other, making it impossible to manufacture a catheter equipped with electrodes spaced at short intervals.

Further, if a stress is applied from the periphery of the electrode to the central axis of the conventional catheter for eliminating such steps, an inner lumen of the catheter will be deformed, causing the same to be subjected to a high shear stress by the insertion of a guidewire or mandrel into the inner lumen of the catheter, thereby resulting in a reduction in operation efficiency in manufacturing the catheter; prolonged operation time; and reduced maneuverability while using catheters in clinical practice.

SUMMARY OF THE INVENTION

In view of the problems described above, the present invention provides a catheter capable of utilizing guidewires, having an excellent in maneuverability during insertion into a blood vessel, and capable of being produced with a smaller external diameter compared to conventional catheters, thus allowing insertion up to more peripheral blood vessels, thereby enabling more peripheral pacing and/or mapping. The catheter has electrodes that are narrowly spaced, and includes no steps between sections provided with electrodes and those without electrodes, thus providing an enhanced-safety catheter and a highly efficient production method of making the same.

Means for Solving the Problems

According to an embodiment of the present invention, there is provided a multiple-electrode monorail guide catheter for use in vascular insertion. The catheter includes an elongated catheter main body having a proximal end and a distal end; a guidewire inlet opening formed on the distal end; an electrode assembly; a guidewire outlet opening; an operation tube portion; and a terminal unit provided on the proximal end. The electrode assembly has a double-lumen structure composed of an outer tube with electrodes provided on an outer surface thereof; and an inner tube for inserting a guidewire therethrough. An outer diameter of said inner tube is smaller than an inner diameter of said outer tube, and the inner tube is inserted through a lumen of said outer tube. The outer tube and said inner tube are independent from each other. A clearance is formed between a luminal surface of said outer tube and an outer circumferential surface of said inner tube. The outer tube has thoughholes at electrode attaching sites for lead wire insertion, and inserted through the lumen of said outer tube are lead wires that are located outside said inner tube and extend from the electrodes to said terminal unit on the proximal end.

There may be provided the catheter, wherein steps are not formed between the outer surface of said outer tube and outer surfaces of the electrodes.

There may be provided the catheter, wherein 2 to 40 electrodes are embedded in an outer surface of said electrode assembly.

There may be provided the catheter, wherein an interval between the electrodes is 0.10 to 10 mm.

There may be provided the catheter, wherein an outer diameter of said electrode assembly is 0.50 to 2.0 mm.

There may be provided the catheter, wherein the electrodes are ones used to perform pacing and/or mapping.

There may be provided the catheter, wherein the peripheral vessels are coronary arteries or coronary veins.

There may be provided the catheter, wherein the electrodes are cardiac catheterization electrodes for use in potential measurement in the heart, confirmation of cardiac impulse conducting systems and confirmation of developmental mechanisms of tachycardia circuits, in cardiac electrophysiological testing.

The present invention further provides a method of manufacturing the catheter, the method including:

a step of attaching the electrodes to the outer tube of the catheter, the step including:

welding lead wires to an inner surface of a distal electrode serving as a guidewire inlet opening and to an inner surface of each electrode of the electrode assembly respectively;

inserting the lead wires into the lumen of the outer tube via the through holes that are bored at locations where the electrodes are installed on the outer tube; and mounting the electrodes to the outer tube of the catheter, a step of inserting a mandrel through the lumen of the outer tube to which the electrodes have been attached;

a step of eliminating steps defined by differences in level between the surfaces of the electrodes and the outer circumferential surface of the catheter outer tube, by applying a pressure to the outer tube through which the mandrel is inserted from the outer circumferential side thereof toward the central axis thereof;

a step of removing the mandrel from the outer tube;

a step of inserting the lead wires connected to the electrodes through the lumen of the operation tube;

a step of welding the operation tube to a double-lumen tube composed of the outer tube equipped with the electrodes and the inner tube used for inserting the guidewire to form the guidewire inlet opening; and a step of connecting each of the lead wires connected to the electrodes to a terminal of an electrode potential monitor, in a proximal opening portion of the operation tube.

Effects of the Invention

The catheter according to the present invention permits high security usage of a catheter: capable of utilizing guidewires and having excellent maneuverability during insertion into a blood vessel; having smaller external diameter so as to permit insertion up to more peripheral blood vessels; allowing more peripheral pacing and/or mapping; having electrodes that are narrowly spaced with each other; and having no steps on sections provided with or without electrodes. Further, the present invention provides highly efficient production method of making the same.

BRIEF DESCRIPTION OF THE DRAWING

FIG. 3A illustrates a front view of the catheter according to the present invention;

FIG. 3B illustrates an enlarged view of a guidewire inlet opening;

FIG. 4 illustrates a front view illustrating an enlarged view of an electrode assembly of the catheter according to the present invention;

FIG. 5 illustrates the guidewire inlet opening located at a distal end of the catheter, according to the present invention, when viewed from the distal side thereof;

FIG. 6 illustrates cross sectional view of the catheter which is sectioned at the position of A as illustrated in FIG. 4;

FIGS. 7A and 7B are explanatory drawings of the catheter at or in the vicinity of an electrode-equipped portion, illustrating how an outer tube equipped with electrodes deforms in the course of embedding electrodes, while an inner tube thereof remains undeformed. Specifically, FIG. 7A illustrates plane views respectively showing the electrode, the outer tube and the inner tube, sequentially from the right to the left, and FIG. 7B illustrates cross sectional view of the catheter at position B where no electrodes is attached thereto;

FIGS. 8A to 8B are explanatory drawings of the catheter at or in the vicinity of the electrode-equipped portion, illustrating how an outer tube equipped with electrodes deforms in the course of embedding the electrodes, while an inner tube thereof remains undeformed. Specifically, FIG. 8A illustrates a coronal sectional view of that shown in FIG. 7A, and FIG. 8B illustrates cross sectional view of the catheter at position C located in the electrode-equipped portion; in the course of installing the electrodes, the outer tube is more deformed as compared to the non-electrode equipped portions shown in FIG. 7B, causing an inner lumen of the outer tube to be narrowly formed, while the inner tube remain unaffected;

MODE FOR CARRYING OUT THE INVENTION

Figure 1:
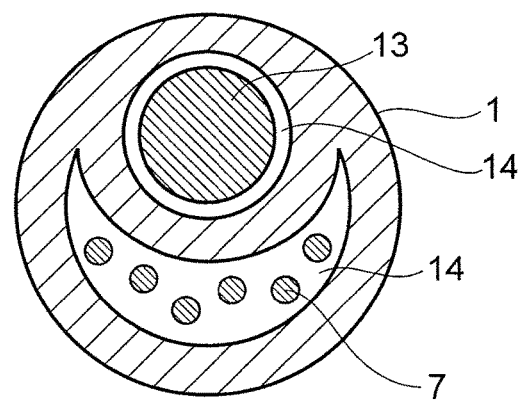
FIG. 1 is an explanatory drawing illustrating a sectional view of a conventional guide catheter for use in peripheral vessels, the catheter sectioned at or in the vicinity of a distal portion of the catheter.
Figure 2:
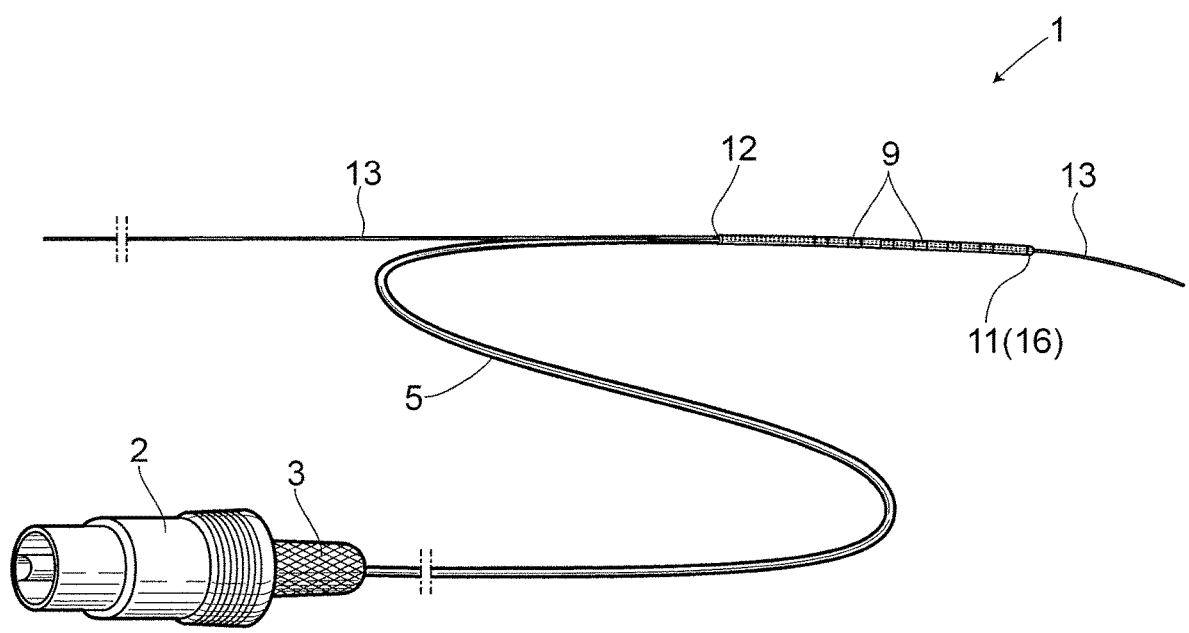
FIG. 2 illustrates a schematic view of the catheter according to the present invention.

The following embodiments of the present invention are only presented as examples, and are not to limit the technical scope of the invention. The technical scope of the invention is only limited by the descriptions in the claims. The present invention may be modified (e.g. an element(s) of the invention may be omitted or replaced, or an additional element(s) may be added to the invention), without departing from the gist of the invention.

All the literatures mentioned in this specification are incorporated in a way such that they are holistically cited.

One embodiment of the present invention is a multiple-electrode monorail guide catheter used for vascular insertion.

The aforementioned catheter has an elongated catheter main body; a proximal end; a distal end; a guidewire inlet opening 16 provided on the distal end; an electrode assembly 9; a guidewire outlet opening 12 (exit); an operation tube portion; and a terminal unit 2 provided on the proximal end. Here, the electrode assembly 9 is formed into a double-lumen structure composed of an outer tube 8 with electrodes 10 provided on the outer surface thereof; and an inner tube 6 for inserting a guidewire therethrough. An outer diameter of the inner tube 6 is smaller than an inner diameter of the outer tube 8, and the inner tube 6 is inserted through the lumen of the outer tube 8. The outer tube 8 and the inner tube 6 are independent from each other, and a clearance is formed between the luminal surface of the outer tube 8 and the outer circumferential surface of the inner tube 6. Inserted through the lumen of the outer tube 8 are lead wires 7 that are located outside the inner tube 6 and extend from the electrodes 10 to the terminal unit 2 on the proximal end.

An electrode is attached to a distal tip end portion of the catheter of the invention. This electrode not only functions as an electrode, but also serves as a guidewire insertion entrance. In this specification, this electrode provided on the distal end is referred to as a distal electrode 11. Further, in this specification, the electrode assembly 9 refers to a double-lumen portion composed of the outer and inner tubes, except the site at the distal electrode 11; and the guidewire insertion entrance and exit where the inner tube 6 and outer tube 8 are connected to each other. Electrodes other than the distal electrode 11 are embedded in such double-lumen portion as the electrode assembly 9. Therefore, the double-lumen structure of the electrode assembly 9 is configured in a way such that the outer tube 8 and the inner tube 6 are independent from each other, and are not integrally molded together. That is, clearances, gaps or cavities are formed between the outer tube 8 and the inner tube 6; and the luminal surface of the outer tube 8 and the outer circumferential surface of the inner tube 6 are mostly in no contact with each other, even when they are partially in contact with each other.

Further, one purpose of the invention is to prevent the concavities and convexities on the outer surface of a catheter from damaging an intravascular lumen wall by scratch, when inserting the catheter of the invention into a peripheral intravascular lumen. Another purpose of the invention is to prevent an electrode-separation accident from occurring in an intravascular lumen. Therefore, the catheter of the invention is configured in such a way that steps are not formed by the outer surfaces of the electrodes 10; and parts of the outer surface of the outer tube 8 that are not equipped with the electrodes 10. In order to achieve these purposes, the catheter of the invention is manufactured as follows. That is, after attaching the electrodes 10 to the outer tube 8, a pressure is applied from the outer circumferential side of the outer tube 8 toward an axial direction thereof with an inner tube 6 such as a mandrel being present in the lumen of the outer tube 8, thereby allowing the electrodes 10 to be embedded into the outer circumference of the outer tube 8, thus eliminating the steps.

In this specification, the expression that "steps are not formed" by the electrodes 10 and the outer circumferential surface of the outer tube 8, refers to a state where there exists no step; or the steps are so small that an intravascular lumen wall will not be damaged by scratch when inserting the catheter of the invention into the intravascular lumen, even without performing a coating treatment on the catheter.

In this process for eliminating the steps defined by differences in level between the electrodes 10 and the outer circumferential surface of the outer tube 8, the lumen of the part of the outer tube 8 that is equipped with the electrodes 10 deforms and narrows due to a pressure. Here, a clearance is provided between the luminal surface of the outer tube 8 and the outer surface of the inner tube 6 such that the deformation of the outer tube 8 will not affect the shape of the inner tube 6. By providing such clearance between the outer tube 8 and the inner tube 6, the shape of the inner tube 6 will not be affected by the deformation of the outer tube 8 which is caused by the pressure applied from the outer circumference of the electrodes 10 toward a central axis direction during an electrode installation step in the manufacturing process. As a result, with regard to the insertion of a mandrel or guidewire that is to be inserted through the lumen of the inner tube 6, or the insertion of the inner tube 6 into the lumen of the outer tube 8, smooth insertion operations are made possible without a significant shear stress at the time of insertion.

Further, as the insertion operations of such guidewire, mandrel or inner tube 6 become smoother and more efficient, the efficiency in manufacturing a catheter can be improved as well.

Furthermore, with regard to the insertion of the inner tube 6 into the outer tube 8, or the insertion of a mandrel or guidewire into the outer tube 8 or inner tube 6 respectively, spraying a solvent on the surface of a member to be inserted can further lower the shear stress at the time of insertion, and further improve the operation efficiency accordingly.

In fact, as described in working example, the catheter of the invention can be manufactured in about one-third the time of the conventional catheter described in JP2012-75800 (i.e. the manufacturing efficiency has improved three times).

Moreover, since the catheter of the invention has the aforementioned structure, there can be provided a catheter with an outer diameter smaller than that of a conventional catheter. Particularly, the catheter of the invention can be inserted into smaller peripheral vessels into which a conventional catheter could not be inserted to perform pacing and/or mapping. That is, the catheter of the invention allows pacing and/or mapping to be performed even on those smaller peripheral vessels.

Since the catheter of the invention can be inserted into smaller peripheral vessels, a signal source causing arrhythmia can be precisely detected when treating the same, for example, and a disorder can thus be more precisely removed through heat irradiation or a medical agent(s). That is, an area of removal is made smaller such that a patient is able to be treated in a less invasive manner.

Examples of the peripheral vessels in which the catheter of the invention may be used, include the coronary veins and coronary arteries of the heart; and the arteries and veins of the brain, lungs and kidneys.

Further, examples of the target diseases in which pacing and/or mapping of the above peripheral vessels are performed, include but are not limited to arrhythmias such as atrial fibrillation (AF), atrioventricular re-entrant tachycardia (AVRT) and left atrial tachycardia (LAT); and heart failure.

In this specification, when expressing, for example, the length, outer diameter or inner diameter of a catheter with numerical values, a range defined by such numerical values is a numerical value range interpreted by the significant figures of such clearly specified numerical values, as generally understood in the technical field of the present invention. That is, for example, when there is a description that "an outer diameter is 1 mm," it means that the outer diameter is in a range of 0.6 to 1.4 mm; and when there is a description that "an outer diameter is 1.0 mm," it means that the outer diameter is in a range of 0.96 to 1.04 mm.

Further, these numerical values may appear after the expression "about." In such case, a numerical value following the expression "about" is considered to have a numerical value range interpreted by the significant figures thereof as above. That is, for example, when there is a description that "an outer diameter is about 1 mm," it means that the outer diameter is in a numerical value range of 0.6 to 1.4 mm; and when there is a description that "an outer diameter is about 1.0 mm," it means that the outer diameter is in a range of 0.96 to 1.04 mm.

Moreover, the operability of a catheter affects the time for performing intravascular insertion. A poor operability leads to a longer time required to perform insertion, which forces a patient to bear the burden. Since the catheter of the invention which is to be inserted into peripheral vessels requires a high operability, the catheter as a guide catheter using a guidewire requires a lumen for inserting a guidewire therethrough. Here, as a guidewire to be inserted into small vessels, a guidewire with an outer diameter of 0.36 mm (0.014 inch) is used most frequently.

There are also manufactured and supplied guidewires having outer diameters of 0.30 mm (0.012 inch) and 0.25 mm (0.01 inch) which are smaller than the above outer diameter. However, these guidewires has a little stiffness, and are thus not used in a practical setting.

It is an object of the invention to allow a catheter to be inserted into smaller peripheral vessels, and eliminate the concavities and convexities on the outer surface of a catheter that occur at the time of installing electrodes 10. Therefore, the present invention has a step of applying a pressure to the electrodes 10 from their outer circumferential direction toward an inner center thereof; and the clearance is provided between the outer tube 8 lumen and the inner tube exterior such that the inner tube 6 will not be deformed during the step of applying the pressure from the outer circumferential side of the electrodes 10 toward the central axis thereof, and that a guidewire is thus able to be smoothly inserted through and removed from the lumen of the inner tube 6. Further, lead wires 7 are inserted through the clearance between the outer tube 8 lumen and the inner tube exterior.

That is, with regard to the abovementioned catheter of the invention, the inner tube 6 will not be deformed into, for example, an elliptical shape, and the electrodes 10 will still maintain their shapes, even after the step where the pressure is applied to the electrode-equipped outer tube 8 from the outer circumferential side thereof toward the central axis thereof to embed the electrodes 10 into the outer circumference of the catheter and then to eliminate the steps defined by differences in level between the outer circumferential surfaces of the outer tube 8 and the electrodes 10. Particularly, as a guidewire slides in the inner tube lumen, an area of contact between the outer circumference of the guidewire and the inner tube lumen is small such that a shear stress will not occur between the guidewire and an inner tube, or that a shape of a small circular section will be maintained.

In order to obtain a catheter having such properties and structures, certain restrictions have to be imposed on the ranges of the outer and inner diameters of the outer tube 8; outer and inner diameters of the inner tube 6; and the width of the clearance between the outer tube 8 lumen and the inner tube exterior.

The outer diameter of the electrode assembly 9 of a conventional catheter is about 0.98 to about 3.4 mm. However, the outer diameter of the electrode assembly 9 of the catheter of the present invention is about 0.50 to about 2.0 mm, preferably about 0.60 to about 1.5 mm, most preferably about 0.85 to about 1.1 mm. Thus, there may be provided a catheter of the invention whose electrode assembly 9 has an outer diameter of about 0.80 to about 0.98 mm.

For example, when the outer diameter of the outer tube 8 is about 0.90 mm, the inner diameter thereof is about 0.70 mm, the outer diameter of the inner tube 6 is about 0.50 to 0.60 mm, the outer diameter of the electrode assembly 9 is about 1.0 mm, the inner diameter of the electrode assembly 9 is about 0.90 mm, the outer diameter of the electrode assembly 9 after eliminating the steps defined by differences in level between the electrodes 10 and catheter outer circumference by applying a pressure thereto is 0.90 mm, the inner diameter of the electrode assembly 9 after eliminating the steps defined by differences in level between the electrodes 10 and catheter outer circumference by applying a pressure thereto is 0.80 mm, and the outer diameter of a lead wire is in a range of about 0.05 to about 0.10 mm where the outer diameter of a lead wire is typically about 0.08 mm. Further, the width of the clearance between the outer tube lumen and the inner tube exterior is in a range of about 0.05 to about 0.2 mm.

As such electrodes, there can be used, for example, pipe-shaped or coil-shaped electrodes.

Moreover, since there exists no step in the electrode assembly 9 of the catheter of the invention, that is often formed by the electrodes 10 and the non-electrode equipped portions, a resin is not required to be applied to the step portion as conventionally applied, thereby making it possible to manufacture a catheter with a narrower interval between the electrodes 10. Possible electrode intervals include a range of about 0.10 to about 200 mm, a range of about 0.10 to about 0.15 mm, a range of about 0.10 to about 0.20 mm, a range of about 0.10 to about 0.25 mm, a range of about 0.15 to about 0.20 mm, a range of about 0.15 to about 0.25 mm, a range of about 0.20 to about 0.25 mm, a range of about 0.25 to about 5 mm or a range of about 0.50 to about 5 mm.

Particularly, the electrode interval can be made smaller if using coil-shaped electrodes.

Regardless of a pipe-shaped electrode or a coil-shaped electrode, the width of such electrode is about 0.30 to about 4.0 mm, preferably about 0.40 to about 3.0 mm, most preferably about 0.50 to about 2.0 mm. The outer diameter of the electrode is, for example, about 1.0 mm, and the inner diameter thereof is about 0.90 mm.

Since the electrode interval can thus be made small, a number of electrodes can be installed highly densely. The number of the electrodes that can be attached to one catheter of the invention is 2 to 40, preferably 4 to 30, most preferably 6 to 20.

In the case of the catheter of the present invention, the length from the guidewire inlet opening 16 to the guidewire outlet opening 12, including the electrode assembly 9 (i.e. double-lumen portion), is in a range of about 130 to about 400 mm, preferably a range of about 140 to 350 mm, most preferably about 200 mm.

The entire length of the catheter of the invention is in a range of about 500 to about 2,000 mm, most preferably about 1,300 mm.

The length of the operation tube 5 is in a range of about 100 to about 1,900 mm; and the outer diameter thereof is in a range of about 0.5 to about 1.6 mm, preferably in a range of about 0.6 to about 0.8 mm.

As for the lead wires 7, a resin is applied to the outer circumferences thereof. And, there are used, for example, lead wires 7 whose outer circumferential surfaces have been insulated. Here, the outer diameter of the lead wires 7 is about 0.08 mm, and the lead wires 7 are inserted through the lumens of the double-lumen portion and the operation tube portion, ranging from the electrodes to the terminal unit 2 of the catheter proximal end portion.

In the double-lumen portion, the lead wires 7 are inserted through the lumen of the outer tube 8 and outside the inner tube 6, from the electrodes 10 toward the proximal end. In the operation tube 5, the lead wires 7 are inserted through the lumen thereof, and are connected to, for example, a cardiac electrophysiological observation/monitoring device, a pacing/sensing analyzer or a pulse generator, through the terminal unit 2 at the proximal end.

Further, one embodiment of the present invention is a method for manufacturing the above catheter of the invention.

The above catheter can be manufactured through the following steps which are a step of attaching the electrodes 10 to the outer tube 8 of the catheter, by inserting lead wires 7 that are already welded to an inner surface of the distal electrode 11 and the electrodes 10 to be attached to the electrode assembly 9 into the outer tube lumen via holes 15 that are bored at locations where the electrodes are installed on the outer tube 8;

a step of inserting the mandrel through the lumen of the outer tube 8 to which the electrodes 10 have been attached;

a step of eliminating the steps that are formed between the surfaces of the electrodes 10 and the outer circumferential portion of the catheter outer tube, by applying a pressure to the outer tube 8 to which the electrodes 10 have been attached from the outer circumferential side thereof toward the central axis thereof;

a step of removing the mandrel from the outer tube 8;

a step of inserting the lead wires 7 connected to the electrodes 10 through the lumen of the operation tube 5;

a step of thermally bonding the operation tube 5 and the double-lumen tube composed of the outer tube 8 equipped with the electrodes 10 and the inner tube 6 used for inserting the guidewire, where a proximal opening portion of the inner tube 6 is maintained open while performing bonding such that the proximal opening portion will become the opening portion of guidewire insertion part; and a step of connecting each of the lead wires 7 connected to the electrodes 10 to a terminal 2 of an electrode potential monitor, in a proximal opening portion of the operation tube 5.

With regard to the above-described catheter of the invention, although the outer tube 8 and the inner tube 6 are welded together at the entrance and exit for use in guidewire insertion, the electrode assembly 9 therebetween has the double-lumen structure, and a clearance is provided between the inner tube 6 and the outer tube 8. Further, the electrodes 10 are to be attached to the outer surface of the outer tube 8, and a pressure is applied from the outside toward the inner center thereof so as to eliminate the steps. In the case of a conventional catheter, its lumen will be deformed, narrowed or blocked under such circumstance. Particularly, in the manufacturing process of a conventional catheter, a mandrel or a guidewire could not be smoothly inserted into the inner tube lumen, and the inner tube 6 could not be smoothly inserted into the outer tube lumen, due to an increased shear stress. That is, insertion operations were time-consuming in the manufacturing process of a conventional catheter.

In contrast, when manufacturing the catheter having the structures of the present invention through the above manufacturing method, a little shear stress occurs when inserting the inner tube 6 into the outer tube lumen, and when inserting a mandrel or a guidewire into the inner tube lumen. That is, there can be achieved smooth insertion operations, which contributes to an improvement in the efficiency of manufacturing the catheter.

In addition, the shear stress occurring at the time of performing insertion can be further reduced, and the operation efficiency can thus be improved, by spraying or applying a solvent on a mandrel, a guidewire or the inner tube 6 before inserting the same into a corresponding lumen.

Ethanol or a sterilized water, for example, may be the solvent used when inserting a mandrel, a guidewire or the inner tube 6 into a tube lumen.

Working Example

As an example of the catheter shown in FIG. 2 to FIG. 8, there was manufactured the catheter of the invention by the following method. Particularly, there were employed members by which the entire length of this catheter was made about 1,300 mm, the length of its double-lumen portion was made about 200 mm, the outer and inner diameters of its outer tube 8 were respectively made about 0.90 mm and about 0.66 mm, the outer and inner diameters of its inner tube 6 were respectively made about 0.60 mm and 0.40 mm, and the outer diameter of its opening portion of guidewire insertion part was made about 1.0 mm.

The inner portions of a distal electrode 11 and electrodes 10; and lead wires 7 were welded together through laser welding. Next, the lead wires 7 were inserted into an outer tube lumen through-holes 15 that had already been bored at locations where the electrodes are installed on an outer tube 8, so as to attach the distal electrode 11 to the distal end portion of outer tube of the catheter. Further, a mandrel on which ethanol had been sprayed was inserted through the lumen of the outer tube 8 to which the electrodes 10 had been attached. Later, a pressure was applied to the outer tube 8 to which the electrodes 10 had been attached from an outer circumferential side thereof toward a central axis direction thereof, thus eliminating steps defined by differences in level between the surfaces of the electrodes 10 and the outer circumferential portion of the catheter outer tube. Next, the mandrel was removed from the outer tube 8. In addition, ethanol was sprayed on an inner tube 6 for inserting a guidewire therethrough, followed by inserting such inner tube 6 through the lumen of the outer tube 8. Next, the lead wires 7 connected to the electrodes 10 were inserted through the lumen of an operation tube 5. Later, the operation tube 5; and a double-lumen tube composed of the outer tube 8 already equipped with the electrodes 10 and the inner tube 6 used for inserting the guidewire, were bonded together using a high-frequency heat generating device. At that time, the proximal opening portion of the inner tube 6 was maintained open while performing bonding, such that the proximal opening portion will become the exit opening of the guidewire insertion part. Next, each of the lead wires connected to the electrodes 10 was connected to a terminal 2 of an electrode potential monitor through a connector portion, in a proximal opening portion of the operation tube 5.

As a result of manufacturing the catheter of the invention through the above method, there was obtained a catheter having an outer diameter of 0.90 mm which was smaller than that of the conventional catheter (minimum outer diameter: 0.98 mm) described in JP2012-75800. Here, the catheter of the invention can be manufactured in about one-third of the time of such conventional catheter, i.e., the manufacturing efficiency is improved three times in the case of the catheter of the present invention.

Figure 9:
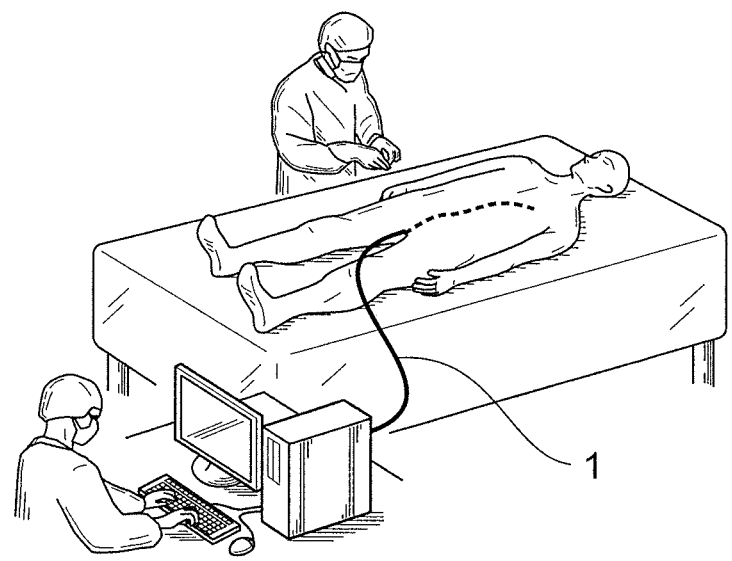
FIG. 9 illustrates how the catheter of the present invention is to be used. The figure illustrates how the catheter is inserted through femoral vein up to heart in order to perform pacing and/or mapping from the outside.
Figure 10:
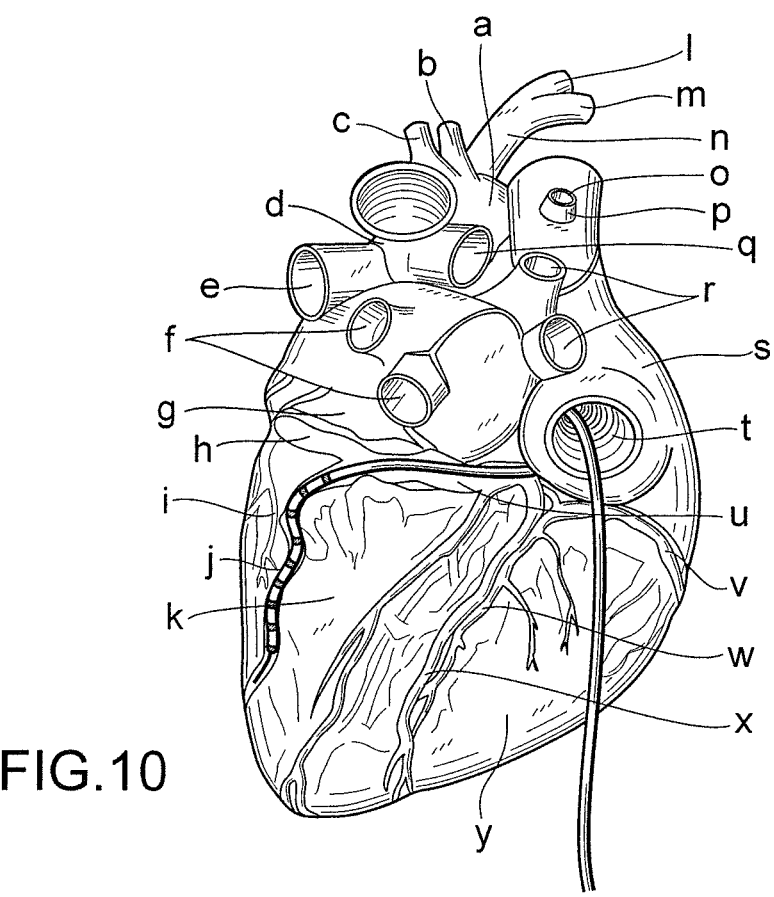
FIG. 10 illustrates how the catheter of the present invention is to be used. The figure illustrates how the catheter of the present invention is inserted from vascular system in posterior surface of the heart and postcaval vein, through right atrial and coronary sinus to coronary veins. The following symbols "a" to "y" illustrates, a: aortic arc, b: left common carotid artery, c: left subclavian artery, dligamentum arteriosum, e: left pulmonary artery, f: left pulmonary vein, g: left atrium, h: great cardiac vein, i: circumflex branch, j: posterior vein of left ventricle, k: left ventricle, l: right common carotid artery, m: right subclavian artery, n: brachiocephalic artery, o: azygos vein, p: superior vena cava, q: right pulmonary artery, r: right pulmonary vein, s: right atrial, t: postcaval vein, u: coronary sinus, v: right coronary artery, w: posterior interventricular branch, x: middle cardiac vein, y: right ventricle.

The catheter of the present invention is used in the following manner when, for example, performing pacing and/or mapping on the coronary veins of the heart. However, the catheter of the invention may also be used in a different manner when performing such procedures (see FIG. 9 and FIG. 10)

1. One femoral vein is approached through skin incision.
2. A wire guide (catheter introducer kit) is inserted into the lumen of the femoral vein from outside the incision.
3. An amplatz-type guide catheter (guiding catheter or angiographic catheter) is inserted through the wire guide, and brought to the coronary sinus ostium (CS ostium) of the right atrium of the heart.
4. A guidewire is inserted through the lumen of the guide catheter, and then brought to an affected area in a coronary vein or to an observation site (peripheral vessel).
5. By running though the guidewire, the catheter of the invention is inserted from an inner tube opening formed at a distal tip end portion of the catheter, followed by allowing the catheter of the invention to pass through veins from the femoral vein, and the guidewire to thus advance inside the catheter until a proximal tip end portion thereof had entered the catheter. In this way, the electrodes are able to be positioned at the affected site in the coronary vein or in a lumen as the observation site.
6. A terminal unit 2 of the catheter is then connected to, for example, a pulse generator or a pacing system analyzer through an extension cable or the like.
7. Pacing and/or mapping are performed on the affected site in the coronary vein or on the observation site.
8. After performing pacing and/or mapping on the affected site in the coronary vein or on the observation site, the catheter, guidewire and guide catheter are removed in an order opposite to that in which the insertion procedures are performed.
9. The incision above the femoral vein is sutured.

Further, when the catheter of the invention is used to perform pacing and/or mapping on the coronary veins of the heart, there may also be employed methods where instead of the femoral vein, the catheter can be applied through the left or right cephalic vein, the subclavian vein or the internal jugular vein. Normally, the left lateral subclavian vein or the right internal jugular vein is utilized.

What is claimed:

1. A multiple-electrode monorail guide catheter for use in vascular insertion, comprising:
    an elongated catheter main body having a proximal end portion and a distal end portion, said elongated catheter main body extending from the distal end portion toward the proximal end portion, and comprising:
    an electrode assembly defining the distal end portion;
    an operation tube extending from a proximal end of the electrode assembly towards the proximal end portion; and
    a terminal unit at the proximal end portion;
    wherein the electrode assembly has a double-lumen structure composed of:
        a) an outer tube having electrodes provided on an outer surface thereof; and
        b) an inner tube comprising a guidewire inlet opening at a distal end of the inner tube and a guidewire outlet opening at a proximal end of the inner tube for inserting a guidewire therethrough, having an outer diameter smaller than an inner diameter of said outer tube, and being accommodated within a lumen of said outer tube, wherein said outer tube and said inner tube are independently provided from each other, and compose a clearance defined by a luminal surface of the outer tube and an outer circumferential surface of the inner tube;
        c) through-holes bored through the outer tube at locations where the electrodes are installed on the outer tube; and
        d) lead wires extending from the electrodes through the through-holes, the clearance and a lumen formed by the operation tube to the terminal unit on the proximal end portion, said lead wires located outside the inner tube and inserted from the electrodes into the lumen of the outer tube via the through-holes,
    wherein said lead wires are capable of directly contacting a portion of the luminal surface of the outer tube and a portion of the outer circumferential surface of the inner tube, and
    wherein an outer diameter of said electrode assembly is in a range from about 0.50 to about 2.0 mm.

2. The catheter according to claim 1, wherein the electrodes are cardiac catheterization electrodes for use in potential measurement, confirmation of cardiac impulse conducting systems and confirmation of developmental mechanisms of tachycardia circuits, in cardiac electrophysiological testing.

3. The catheter according to claim 1, wherein the luminal surface is formed of a continuous arc.

4. The catheter according to claim 1, wherein the luminal surface is tubular.

5. The catheter according to claim 1, wherein the multiple-electrode monorail guide catheter is free from steps formed between the outer surface of said outer tube and outer surfaces of the electrodes.

6. The catheter according to claim 5, wherein the electrodes are cardiac catheterization electrodes for use in potential measurement, confirmation of cardiac impulse conducting systems and confirmation of developmental mechanisms of tachycardia circuits, in cardiac electrophysiological testing.

7. The catheter according to claim 5, wherein 2 to 40 electrodes are embedded in an outer surface of said electrode assembly.

8. The catheter according to claim 7, wherein the electrodes are ones used to perform pacing and/or mapping.

9. The catheter according to claim 7, wherein the electrodes are cardiac catheterization electrodes for use in potential measurement, confirmation of cardiac impulse conducting systems and confirmation of developmental mechanisms of tachycardia circuits, in cardiac electrophysiological testing.

10. The catheter according to claim 7, wherein an interval between the electrodes is 0.10 to 10 mm.

11. The catheter according to claim 10, wherein the electrodes are ones used to perform pacing and/or mapping.

12. The catheter according to claim 10, wherein the electrodes are cardiac catheterization electrodes for use in potential measurement, confirmation of cardiac impulse conducting systems and confirmation of developmental mechanisms of tachycardia circuits, in cardiac electrophysiological testing.

* * * * *